(12) United States Patent
Posnack et al.

(10) Patent No.: US 11,071,597 B2
(45) Date of Patent: Jul. 27, 2021

(54) TELEMEDICINE FOR ORTHOPEDIC TREATMENT

(71) Applicant: ROM TECHNOLOGIES, INC., Brookfield, CT (US)

(72) Inventors: Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US); Steven Mason, Las Vegas, NV (US)

(73) Assignee: ROM TECHNOLOGIES, INC., Brookfield, CT (US)

(*) Notice: Subject to any disclaimer, the term of this patent is extended or adjusted under 35 U.S.C. 154(b) by 0 days.

(21) Appl. No.: 17/021,895

(22) Filed: Sep. 15, 2020

(65) Prior Publication Data
US 2021/0100628 A1    Apr. 8, 2021

Related U.S. Application Data

(60) Provisional application No. 62/910,232, filed on Oct. 3, 2019.

(51) Int. Cl.
*A61B 34/10* (2016.01)
*A61B 34/00* (2016.01)
(Continued)

(52) U.S. Cl.
CPC .............. *A61B 34/25* (2016.02); *A61B 34/10* (2016.02); *G16H 20/40* (2018.01); *G16H 40/40* (2018.01);
(Continued)

(58) Field of Classification Search
CPC ... A61B 34/25; A61B 34/10; A61B 2034/105; A61B 2034/258; G16H 20/40; G16H 40/67; G16H 40/40
See application file for complete search history.

(56) References Cited

U.S. PATENT DOCUMENTS

| 6,182,029 B1 | 1/2001 | Friedman |
| 6,413,190 B1 | 7/2002 | Wood et al. |

(Continued)

FOREIGN PATENT DOCUMENTS

| CA | 2698078 A1 | 3/2010 |
| CN | 112603295 A | 2/2003 |

(Continued)

OTHER PUBLICATIONS

Claris Healthcare Inc.; Claris Reflex Patient Rehabilitation System Brochure, https://clarisreflex.com/, retrieved from internet on Oct. 2, 2019; 5 pages.

(Continued)

*Primary Examiner* — George Manuel
(74) *Attorney, Agent, or Firm* — Dickinson Wright, PLLC; Stephen A. Mason; Jonathan H. Harder

(57) ABSTRACT

A computer-implemented system includes an assistant interface for providing remote medical assistance to aid a patient in performing various aspects of a rehabilitation regimen for a body part comprising a joint, a bone, or a muscle group. The assistant interface is configured to communicate, via a network connection, a telemedicine signal with the patient interface. The telemedicine signal is configured to control the patient interface and/or a treatment apparatus configured to be manipulated by the patient to perform the rehabilitation regimen. The patient interface and the treatment apparatus are at a patient location geographically separate from a location of the assistant interface. The telemedicine signal includes one or more of an audio signal, an audiovisual (Continued)

signal, an interface control signal for controlling a function of the patient interface, and/or an apparatus control signal for changing an operating parameter of the treatment apparatus.

30 Claims, 9 Drawing Sheets

(51) Int. Cl.
    *G16H 40/67* (2018.01)
    *G16H 20/40* (2018.01)
    *G16H 40/40* (2018.01)

(52) U.S. Cl.
    CPC ........ *G16H 40/67* (2018.01); *A61B 2034/105* (2016.02); *A61B 2034/258* (2016.02)

(56) References Cited

U.S. PATENT DOCUMENTS

| | | | |
|---|---|---|---|
| 6,491,649 B1 | 12/2002 | Ombrellaro |
| 7,169,085 B1 | 1/2007 | Killin et al. |
| 7,209,886 B2 | 4/2007 | Kimmel |
| 7,974,689 B2 | 7/2011 | Volpe et al. |
| 8,751,264 B2 | 6/2014 | Beraja et al. |
| 8,823,448 B1 | 9/2014 | Shen |
| 9,311,789 B1 | 4/2016 | Gwin |
| 9,312,907 B2 | 4/2016 | Auchinleck et al. |
| 9,919,198 B2 | 3/2018 | Romeo et al. |
| 9,939,784 B1 | 4/2018 | Berardinelli |
| 10,130,298 B2 | 11/2018 | Mokaya et al. |
| 10,424,033 B2 | 9/2019 | Romeo |
| 2003/0036683 A1 | 2/2003 | Kehr et al. |
| 2006/0064329 A1 | 3/2006 | Abolfathi et al. |
| 2009/0011907 A1 | 1/2009 | Radow et al. |
| 2009/0070138 A1 | 3/2009 | Langheier et al. |
| 2010/0268304 A1 | 10/2010 | Matos |
| 2011/0172059 A1 | 7/2011 | Watterson et al. |
| 2011/0218814 A1 | 9/2011 | Coats |
| 2012/0065987 A1 | 3/2012 | Farooq et al. |
| 2012/0190502 A1 | 7/2012 | Paulus et al. |
| 2012/0310667 A1 | 12/2012 | Altman et al. |
| 2013/0123667 A1 | 5/2013 | Komatireddy et al. |
| 2013/0296987 A1 | 11/2013 | Rogers et al. |
| 2014/0006042 A1 | 1/2014 | Keefe et al. |
| 2014/0188009 A1 | 7/2014 | Lange et al. |
| 2014/0194250 A1 | 7/2014 | Reich et al. |
| 2014/0257837 A1 | 9/2014 | Walker et al. |
| 2014/0322686 A1 | 10/2014 | Kang |
| 2015/0088544 A1 | 3/2015 | Goldberg |
| 2015/0161331 A1 | 6/2015 | Oleynik |
| 2015/0339442 A1 | 11/2015 | Oleynik |
| 2016/0140319 A1 | 5/2016 | Stark et al. |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2017/0004260 A1 | 1/2017 | Moturu et al. |
| 2017/0143261 A1 | 5/2017 | Wiedenhoefer et al. |
| 2017/0147789 A1 | 5/2017 | Wiedenhoefer et al. |
| 2017/0181698 A1 | 6/2017 | Wiedenhoefer et al. |
| 2017/0243028 A1 | 8/2017 | LaFever et al. |
| 2017/0265800 A1 | 9/2017 | Auchinleck et al. |
| 2017/0278209 A1 | 9/2017 | Olsen et al. |
| 2017/0300654 A1* | 10/2017 | Stein ...................... H01Q 21/28 |
| 2017/0329917 A1 | 11/2017 | McRaith et al. |
| 2017/0344726 A1 | 11/2017 | Duffy et al. |
| 2017/0360586 A1 | 12/2017 | Dempers et al. |
| 2018/0052962 A1 | 2/2018 | Van Der Koijk et al. |
| 2018/0071572 A1 | 3/2018 | Gomberg et al. |
| 2018/0085615 A1 | 3/2018 | Astolfi et al. |
| 2018/0102190 A1 | 4/2018 | Hogue et al. |
| 2018/0240552 A1 | 8/2018 | Tuyl et al. |
| 2018/0271432 A1 | 9/2018 | Auchinleck et al. |
| 2018/0280784 A1 | 10/2018 | Romeo et al. |
| 2018/0330824 A1 | 11/2018 | Athey et al. |
| 2019/0019578 A1 | 1/2019 | Vaccaro |
| 2019/0066832 A1 | 2/2019 | Kang et al. |
| 2019/0167988 A1 | 6/2019 | Shahriari et al. |
| 2020/0143922 A1 | 5/2020 | Chekroud et al. |
| 2020/0151595 A1 | 5/2020 | Jayalath et al. |
| 2020/0152339 A1 | 5/2020 | Pulitzer et al. |
| 2020/0160198 A1 | 5/2020 | Reeves et al. |
| 2020/0176098 A1 | 6/2020 | Lucas et al. |
| 2020/0293712 A1 | 9/2020 | Potts et al. |
| 2020/0401224 A1 | 12/2020 | Cotton |

FOREIGN PATENT DOCUMENTS

| | | |
|---|---|---|
| EP | 3264303 A1 | 1/2018 |
| WO | 2019204876 A1 | 4/2019 |

OTHER PUBLICATIONS

International Searching Authority, Search Report and Written Opinion for International Application No. PCT/US20/51008, dated Dec. 10, 2020; 9 pages.

\* cited by examiner

TELEMEDICINE FOR ORTHOPEDIC TREATMENT

CROSS-REFERENCES TO RELATED APPLICATIONS

This application claims priority to and the benefit of U.S. Provisional Application Patent Ser. No. 62/910,232 filed Oct. 3, 2019, titled "Telemedicine for Orthopedic Treatment," the entire disclosure of which is hereby incorporated by reference for all purposes.

BACKGROUND

Remote medical assistance, or telemedicine, may aid a patient in performing various aspects of a rehabilitation regimen for a body part. The patient may use a patient interface in communication with an assistant interface for receiving the remote medical assistance via audio and/or audiovisual communications.

SUMMARY

A computer-implemented system is provided. The computer-implemented system comprises a patient interface comprising an output device and an input device. The output device is configured to communicate information to a patient regarding the patient's performance of a treatment plan for the patient. The treatment plan comprises a rehabilitation regimen for a body part comprising at least one of a joint, a bone, or a muscle group. The computer-implemented system also comprises a treatment apparatus configured to be manipulated by the patient for performing the rehabilitation regimen upon the body part. The computer-implemented system also comprises an assistant interface remote from the patient interface and configured to communicate, via a network connection, a telemedicine signal with the patient interface. The telemedicine signal comprises one of an audio signal, an audiovisual signal, an interface control signal for controlling a function of the patient interface, or an apparatus control signal for changing an operating parameter of the treatment apparatus.

A system for remote treatment is also provided. The system for remote treatment comprises a patient interface having an output device and an input device for communicating information to and from a patient. The system for remote treatment also comprises a treatment apparatus configured to be manipulated by the patient for performing a rehabilitation regimen upon the body part, with the body part comprising at least one of a joint, a bone, or a muscle group. The system for remote treatment also comprises an assistant interface configured to communicate a telemedicine signal with the patient interface via a network connection, the telemedicine signal configured to control one of the patient interface or the treatment apparatus. The patient interface and the treatment apparatus are each configured to operate from a patient location geographically separated from the assistant interface.

An assistant user interface generated by a computer is also provided. The assistant user interface comprises an apparatus control having an apparatus status display and an apparatus session control configured to adjust an operating parameter of a treatment apparatus. The treatment apparatus is configured to be manipulated by a patient for performing a rehabilitation regimen upon a body part. The assistant user interface also comprises a patient communications control for controlling an audio or an audiovisual communications session with a patient interface, where the patient interface is configured for use by the patient while performing the rehabilitation regimen upon the body part.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

NOTATION AND NOMENCLATURE

Figure 1:
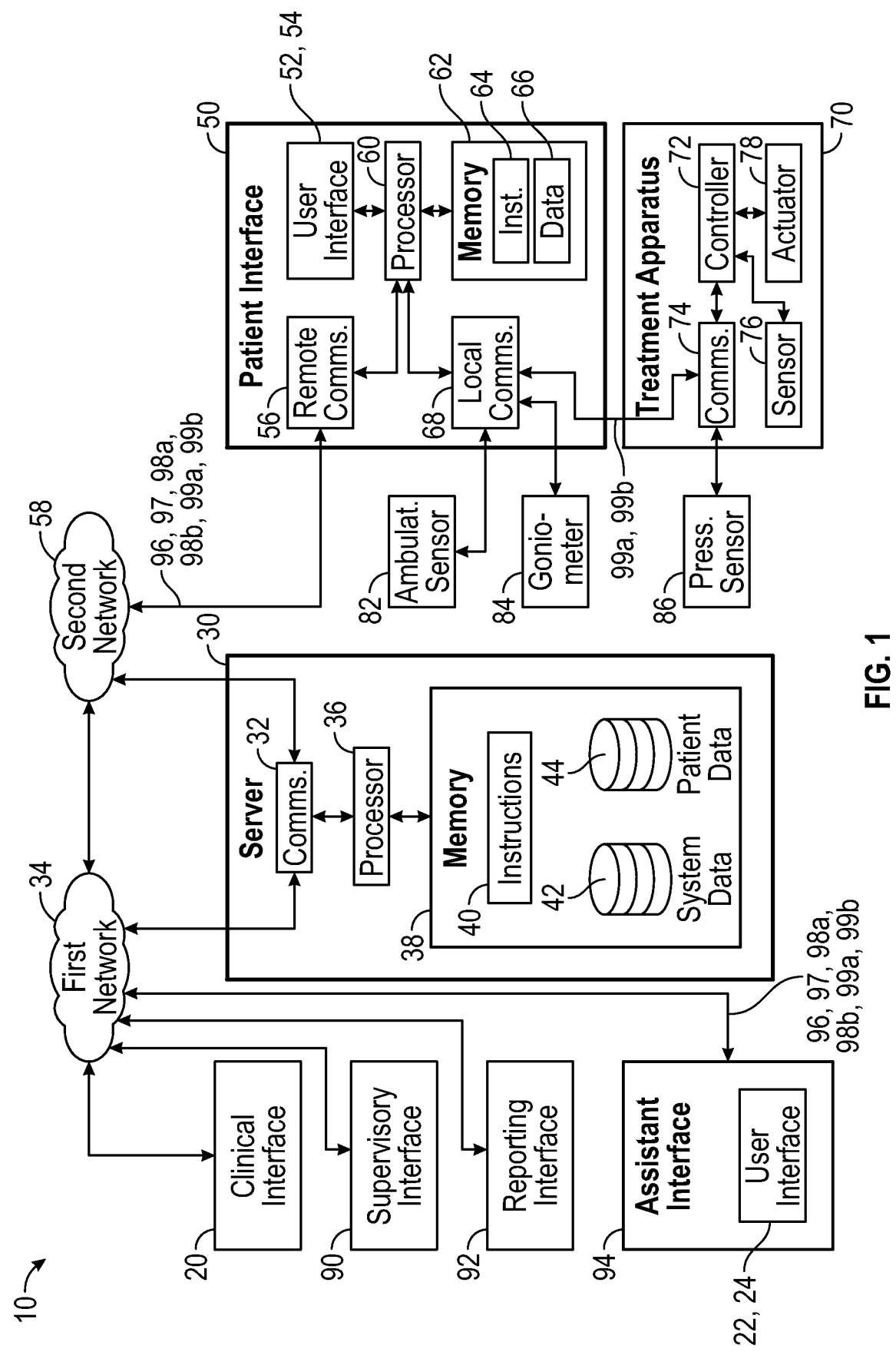
FIG. 1 shows a block diagram of an embodiment of a computer implemented system for managing a treatment plan.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

Moreover, various functions described below can be implemented or supported by one or more computer programs, each of which is formed from computer readable program code and embodied in a computer readable storage medium. The terms "application" and "program" refer to one or more computer programs, software components, sets of instructions, procedures, functions, methods, objects, classes, instances, related data, or a portion thereof adapted for implementation in a suitable computer readable program code. The phrase "computer readable program code" includes any type of computer code, including source code, object code, and executable code. The phrase "computer readable storage medium" includes any type of medium capable of being accessed by a computer, such as read only memory (ROM), random access memory (RAM), a hard disk drive, a flash drive, a compact disc (CD), a digital video disc (DVD), solid state drive (SSD), or any other type of memory. A "non-transitory" computer readable storage medium excludes wired, wireless, optical, or other communication links that transport transitory electrical or other signals. A non-transitory computer-readable storage medium includes media where data can be permanently stored and media where data can be stored and later overwritten, such as a rewritable optical disc or an erasable memory device.

The terms "transmit," "receive," and "communicate," as well as derivatives thereof, encompass both direct and indirect communication. The terms "transmit," "receive," and "communicate," as well as derivatives thereof, encompass both communication with remote systems and communication within a system, including reading and writing to different portions of a memory device. The term "controller" means any device, system or part thereof that controls at least one operation. Such a controller may be implemented in hardware or a combination of hardware and software and/or firmware. The functionality associated with any particular controller may be centralized or distributed, whether locally or remotely.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

The terms telemedicine, telehealth, telemed, teletherapeutic, telemedicine, etc. may be used interchangeably herein.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

FIG. 1 shows a block diagram of a computer-implemented system 10, hereinafter called "the system" for managing a treatment plan. The treatment plan includes one or more treatment protocols, and each treatment protocol includes one or more treatment sessions. Each treatment session comprises several session periods, with each session period including a particular activity for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery.

The system 10 also includes a server 30 configured to store and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for an assistant, such as a doctor, a nurse, a physical therapist, or a technician, to remotely communicate with the patient interface 50 and/or the treatment apparatus 70. Such remote communications may enable the assistant to provide assistance or guidance to a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58. The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for controlling the treatment apparatus 70 (e.g., by changing an operating parameter (a speed of the motor, a resistive force of the pedals, a degree of motion provided by the pedal(s), etc.) of the treatment apparatus 70), an environmental change signal for controlling another electronic device (e.g., thermostat, speaker, light, door, appliance, etc.) that is proximate (e.g., within the same physical space) to the treatment apparatus 70 and/or the patient interface 50, and/or an apparatus monitor signal 99b for monitoring a status of the treatment apparatus 70. In some embodiments, the environmental change signal may cause the electronic device to change a temperature, change an air pressure, change an ambient setting, change an audio setting, etc. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the assistant may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the assistant to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the assistant. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the assistant. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals that may be grouped together, for example, in one or more call centers or at one or more clinicians' offices. In some embodiments, a plurality of assistant interfaces 94 may be distributed geographically. In some embodiments, a person may work as an assistant remotely from any conventional office infrastructure. Such remote work may be performed, for example, where the assistant interface 94 takes the form of a computer and/or telephone. This remote work functionality may allow for work-from-home arrangements that may include part time and/or flexible work hours for an assistant.

Figure 2:
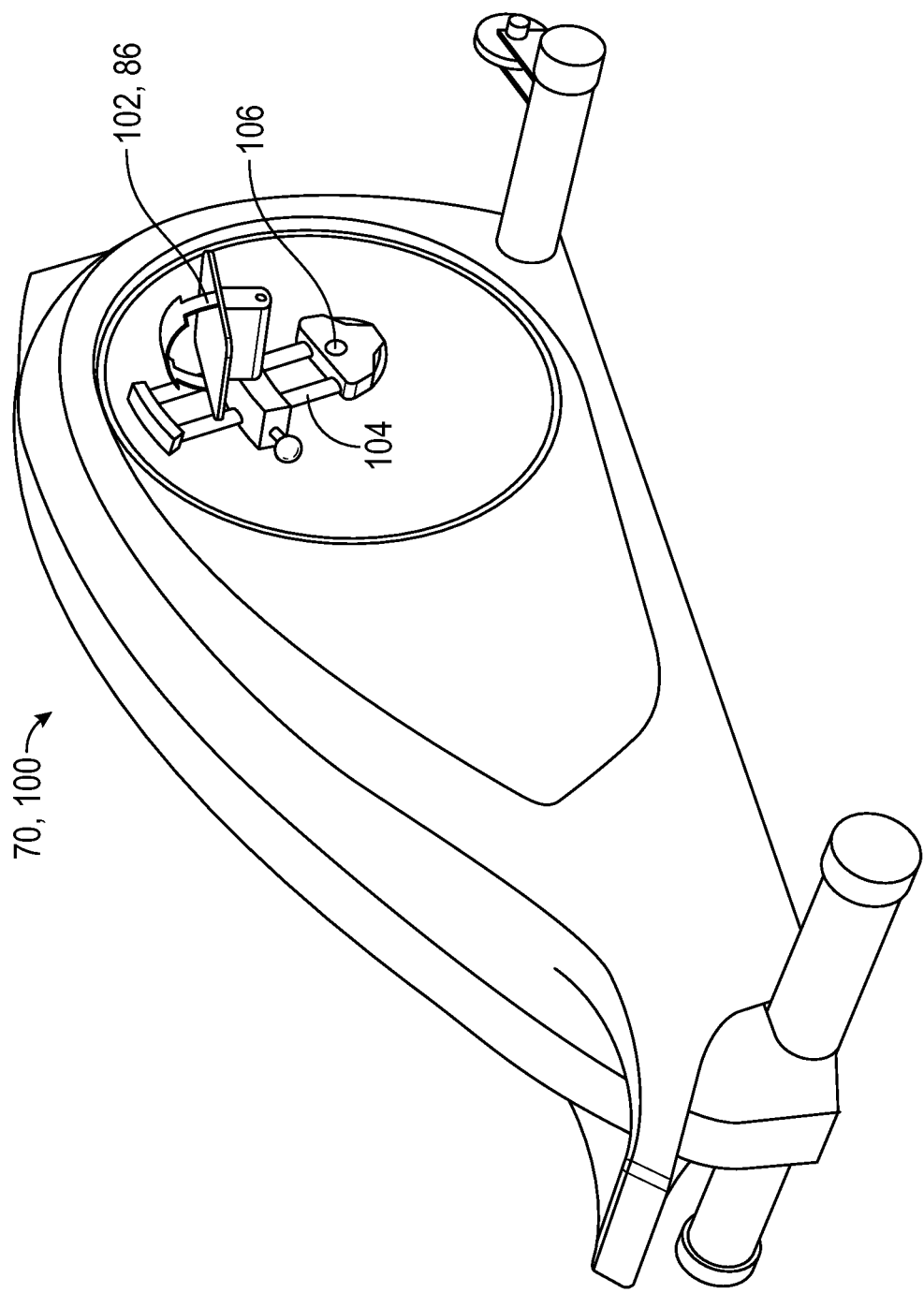
FIG. 2 shows a perspective view of an embodiment of a treatment apparatus.
Figure 3:
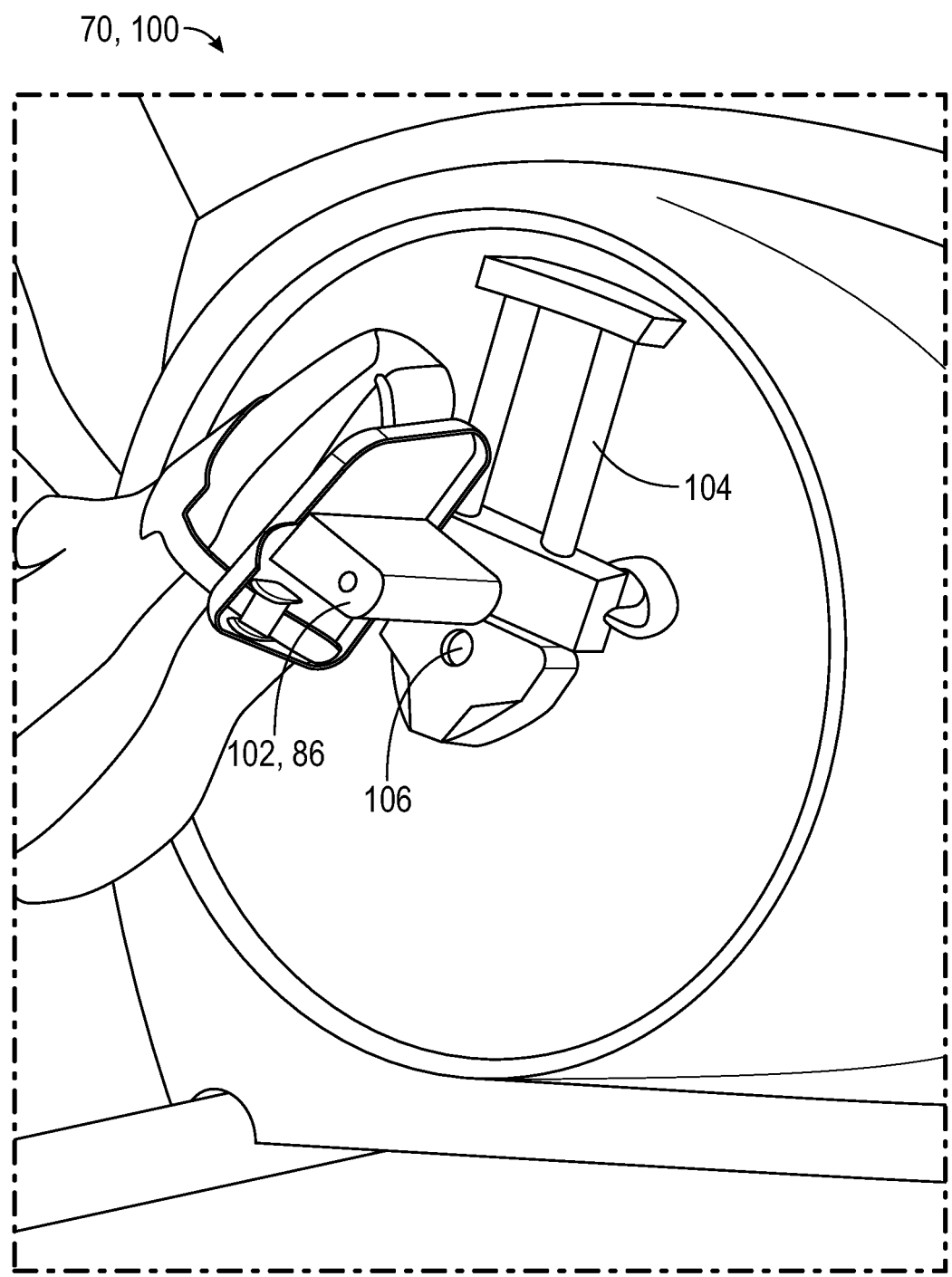
FIG. 3 shows a perspective view of a pedal of the treatment apparatus of FIG. 2.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
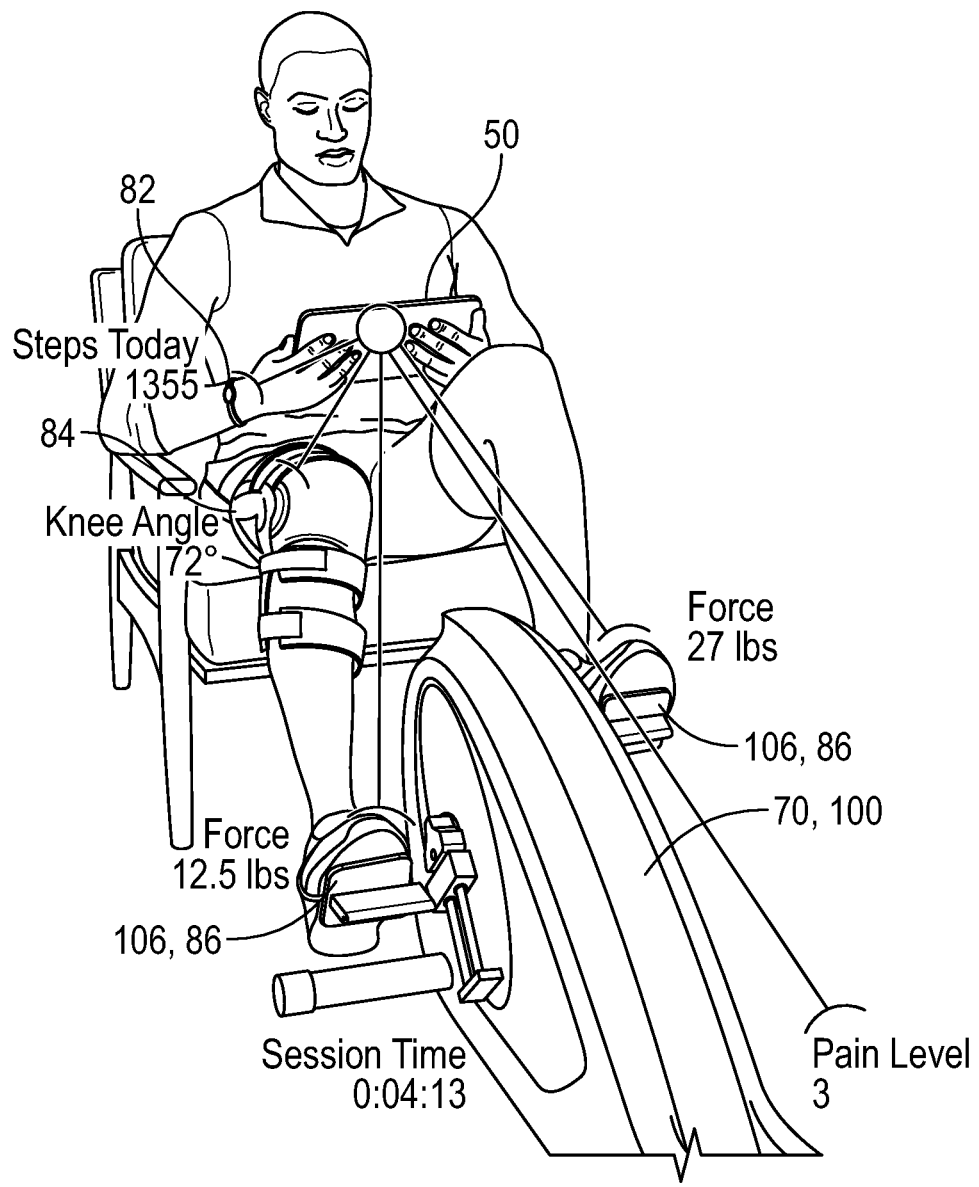
FIG. 4 shows a perspective view of a person using the treatment apparatus of FIG. 2.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patient in response to a solicitation, such as a question, presented upon the patient interface 50.

Figure 5:
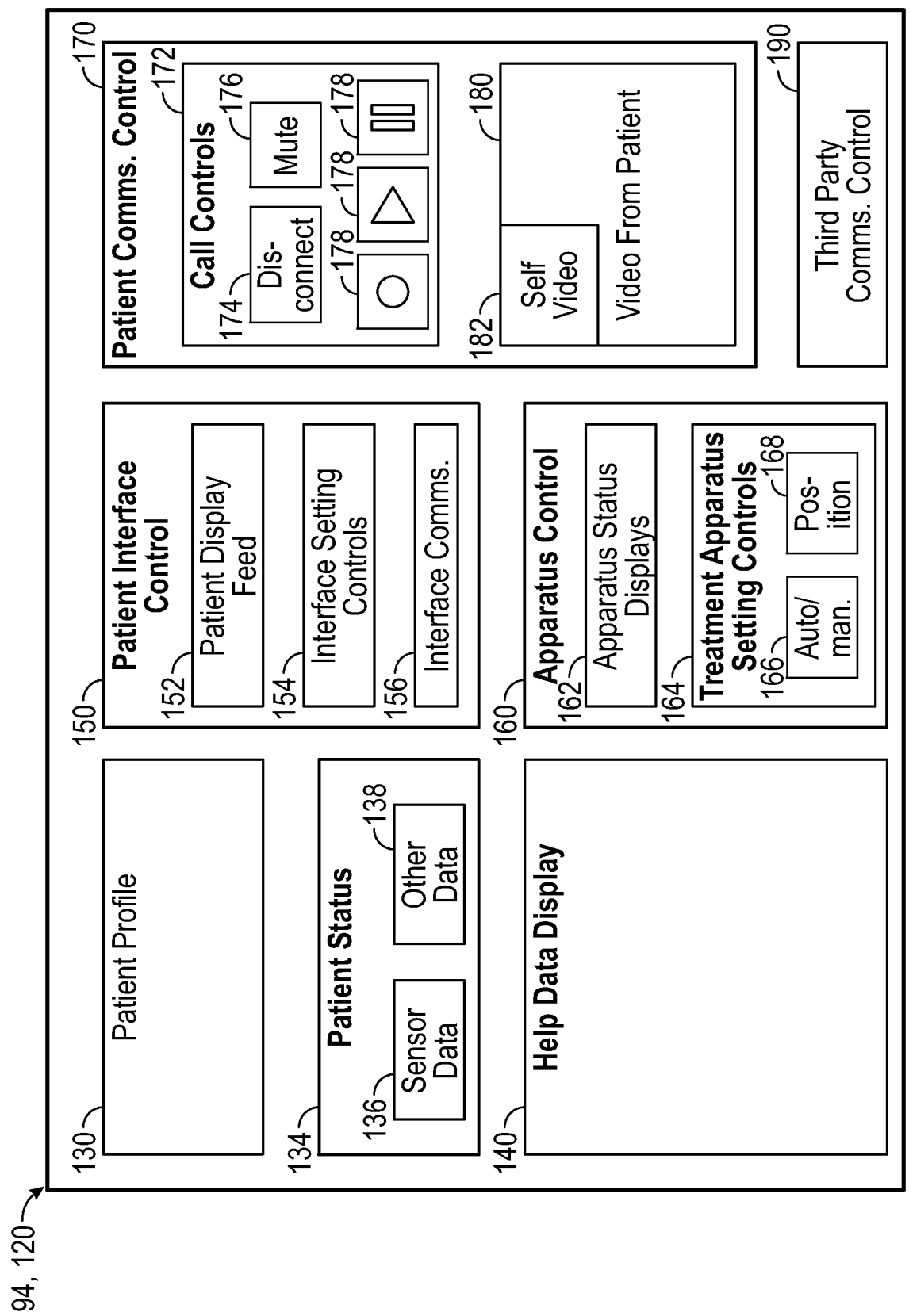
FIG. 5 shows an example embodiment of an overview display of an assistant interface.

FIG. 5 is an example embodiment of an overview display 120 of the assistant interface 94. Specifically, the overview display 120 presents several different controls and interfaces for the assistant to remotely assist a patient with using the patient interface 50 and/or the treatment apparatus 70. This remote assistance functionality may also be called telemedicine.

Specifically, the overview display 120 includes a patient profile display 130 presenting biographical information regarding a patient using the treatment apparatus. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the assistant's need for that information. For example, a medical professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject". In some embodiments, the patient profile display 130 may present information regarding the treatment plan for the patient to follow in using the treatment apparatus 70. Such treatment plan information may be limited to an assistant who is a medical professional, such as a doctor or physical therapist. For example, a medical professional assisting the patient with an issue regarding the treatment regimen may be provided with treatment plan information, whereas a technician troubleshooting an issue with the treatment apparatus 70 may not be provided with any information regarding the patient's treatment plan.

The example overview display 120 shown in FIG. 5 also includes a patient status display 134 presenting status information regarding a patient using the treatment apparatus. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the assistant to use in determining a root cause and/or solution to a patient's problem. In some embodiments, the assistant interface 94 may present two or more help data displays 140, which may be the same or different, for simultaneous presentation of help data for use by the assistant. For example, a first help data display may be used to present a troubleshooting flowchart to determine the source of a patient's problem, and a second help data display may present script information for the assistant to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98*b*. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the assistant to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the assistant to remotely view and/or control the patient interface 50. For example, the patient interface setting control 154 may enable the assistant to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the assistant to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the assistant to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the assistant to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99b. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99 for changing an operating parameter of the treatment apparatus 70, (e.g., a pedal radius setting, a resistance setting, a target RPM, etc.). The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the assistant may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the assistant to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a feed from the assistant interface 94 for presentation by the output device of the patient interface 50. In some embodiments, the feed is live (e.g., real-time or near real-time). In some embodiments, the feed is prerecorded and may be played, paused, fast-forwarded, stopped, and/or replayed. The feed may take the form of an audio feed and/or a video feed. In some embodiments, the patient interface 50 may be configured to provide two-way audio communications, two-way audiovisual communications, two-way visual communications, two-way haptic communications, two-way environmental communications, or two-way communications using on each side of the communications one of the foregoing means, where the means on one side and the means on the other side are different, with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the assistant while the assistant uses the assistant interface 94. Alternatively or additionally, the audio and/or audiovisual communications may include communications with a third party. For example, the system 10 may enable the assistant to initiate a 3-way conversation regarding use of a particular piece of hardware or software, with the patient and a subject matter expert, such as a medical professional or a specialist. The example patient communications control 170 shown in FIG. 5 includes call controls 172 for the assistant to use in managing various aspects of the audio or audiovisual communications with the patient. The call controls 172 include a disconnect button 174 for the assistant to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session. The call controls 172 also include a video feed display 180 for presenting still and/or video images from the patient interface 50, and a self-video display 182 showing the current image of the assistant using the assistant interface. The self-video display 182 may be presented as a picture-in-picture format, within a section of the video feed display 180, as shown in FIG. 5. Alternatively or additionally, the self-video display 182 may be presented separately and/or independently from the video feed display 180.

The example overview display 120 shown in FIG. 5 also includes a third party communications control 190 for use in conducting audio and/or audiovisual communications with a third party. The third party communications control 190 may take the form of a portion or region of the overview display 120, as shown in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a medical professional or a specialist. The third party communications control 190 may include conference calling capability for the third party to simultaneously communicate with both the assistant via the assistant interface 94, and with the patient via the patient interface 50. For example, the system 10 may provide for the assistant to initiate a 3-way conversation with the patient and the third party.

Figure 6:
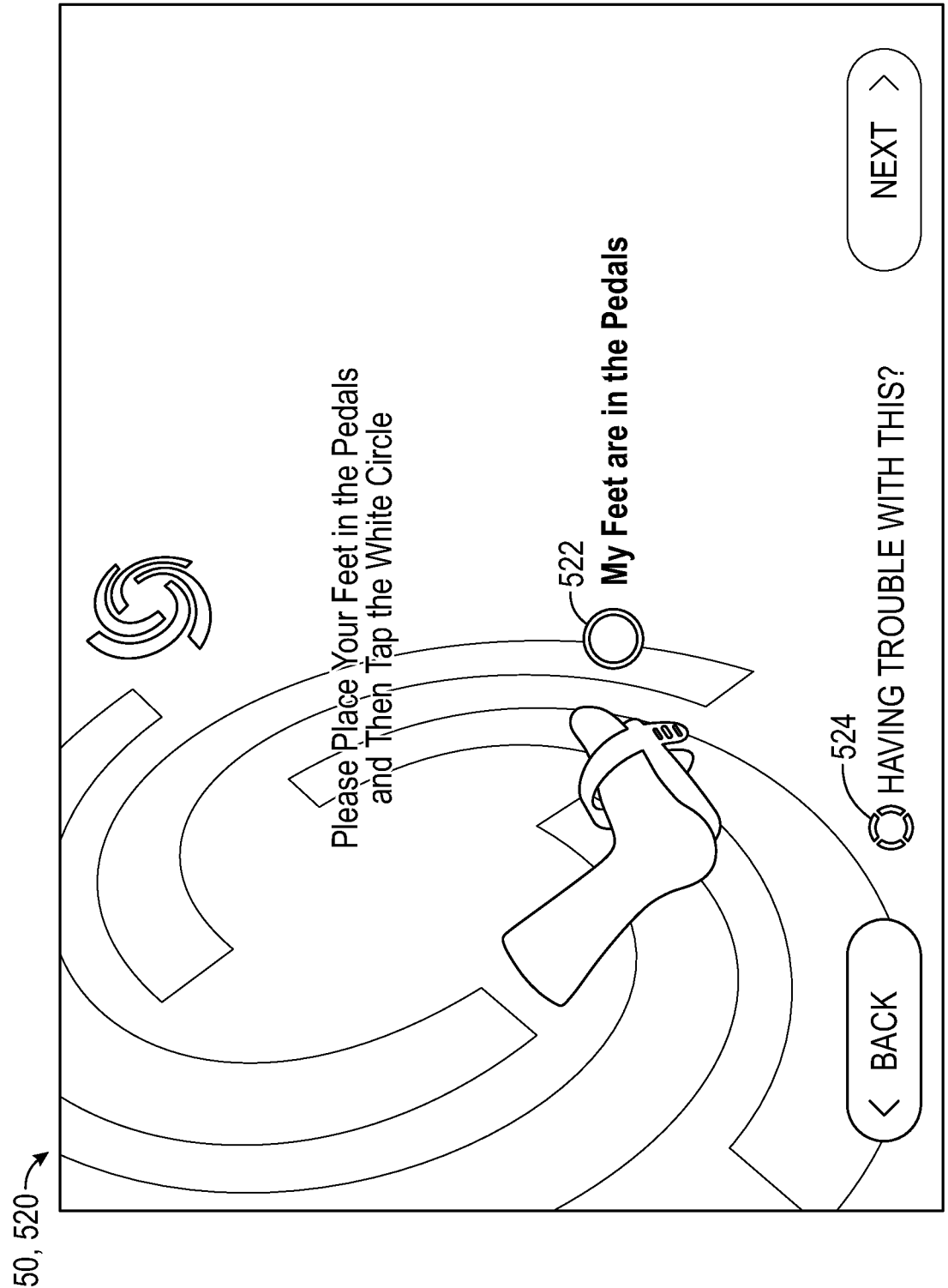
FIG. 6 shows an example embodiment of a positioning confirmation screen of a patient interface.

FIG. 6 shows an example embodiment of positioning confirmation screen 520 of the patient interface 50. This screen 520 is the beginning of a guided walk-through for the patient to use the treatment apparatus 70. Specifically, this screen 520 includes written instructions to guide the patient in placing their feet in the pedals 102 of a stationary cycling machine 100. In some embodiments, this screen 520 may include graphics, such as pictures or animations to help the patient perform particular actions for using the treatment apparatus 70. Screen 520 includes a position confirmation selector 522 for the patient to indicate that they are in position to use the treatment apparatus 70. Screen 520 also includes a trouble button 524 for the patient to indicate that they are having trouble getting in position to use the treatment apparatus 70.

Figure 7:
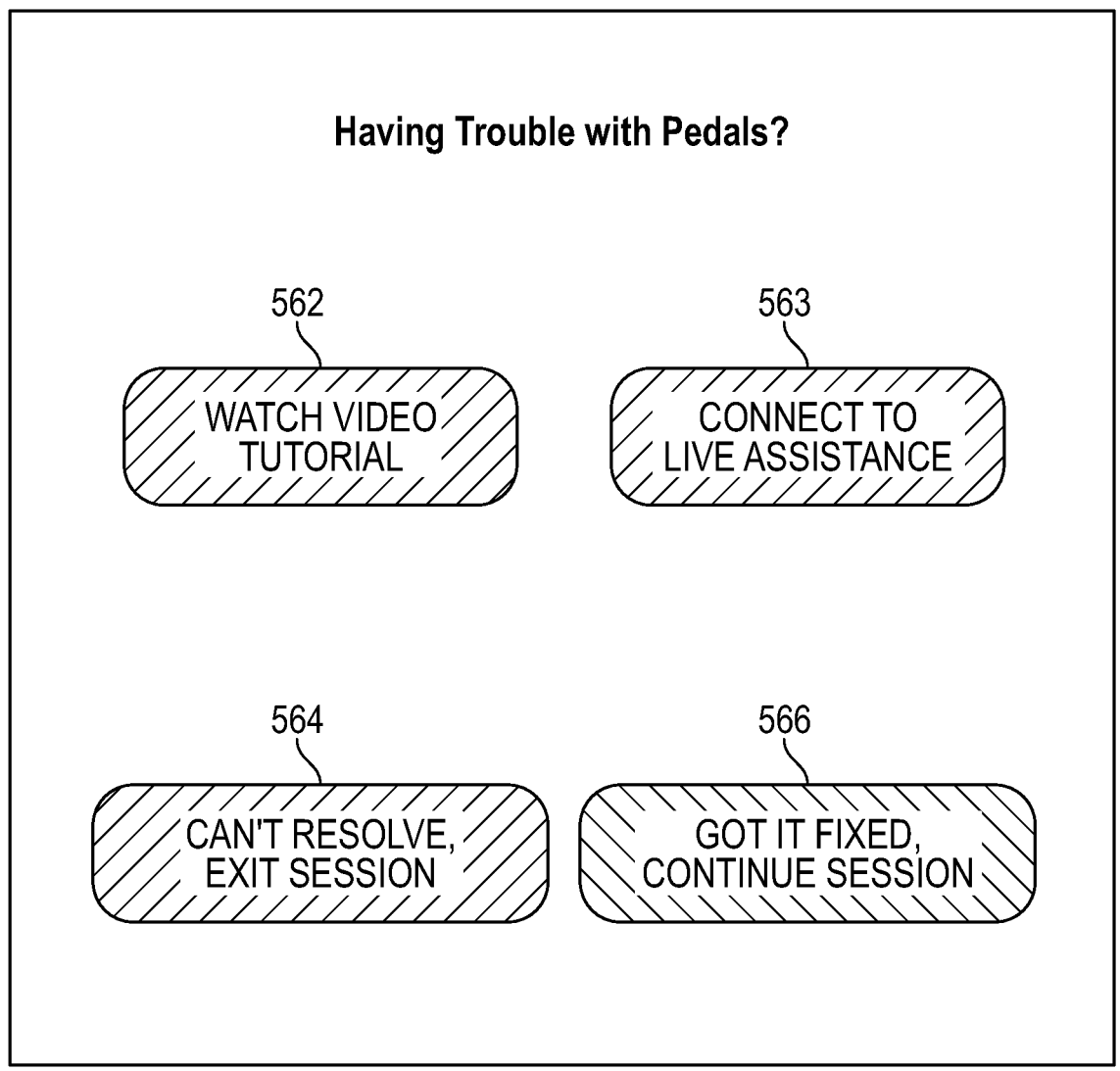
FIG. 7 shows an example embodiment of a positioning help screen of a patient interface; =

FIG. 7 shows an example embodiment of a positioning help screen 560 of the patient interface 50. This positioning help screen 560 may be shown in response to the user selecting the trouble button 524 on the positioning confirmation screen 520. The help screen 560 may automatically be displayed if the patient fails to select the position confirmation selector 522 within a predetermined period of time. In some embodiments, an intermediate screen such as a popup asking if the patient needs more time may be displayed before the help screen 560 is shown. The help screen 560 includes a tutorial request button 562 for the patient to obtain additional prerecorded instructions for using the treatment apparatus 70. The help screen 560 may include a live assistance request button 563 for the patient to initiate a telemedicine session with a remote assistant by using the assistant interface 94.

In some embodiments, an operator or dispatcher may receive an initial request for assistance from the patient interface 50. The operator or dispatcher may forward the request for assistance to an assistant available and/or to an assistant qualified or suited to help the patient with a particular problem or inquiry. For example, medical questions regarding the patient's body may be forwarded to an assistant having medical qualifications, such as a doctor or a nurse. Technical questions regarding operation or use of the treatment apparatus 70 may be forwarded to a technician having training and/or experience with the treatment apparatus 70. In some embodiments, the operator or dispatcher may be equipped and authorized to answer some questions that are frequently asked and/or which do not require specialized knowledge or training.

The help screen 560 may also include an exit button 564 that the patient can use to stop the treatment session in case they are unable to resolve their issue with using the treatment apparatus 70. Use of the exit button 564 may generate an alert to the clinician. The help screen 560 also includes a proceed button 566 that the patient can use to indicate that they have resolved their issue and are able to proceed with the treatment session.

Figure 8:
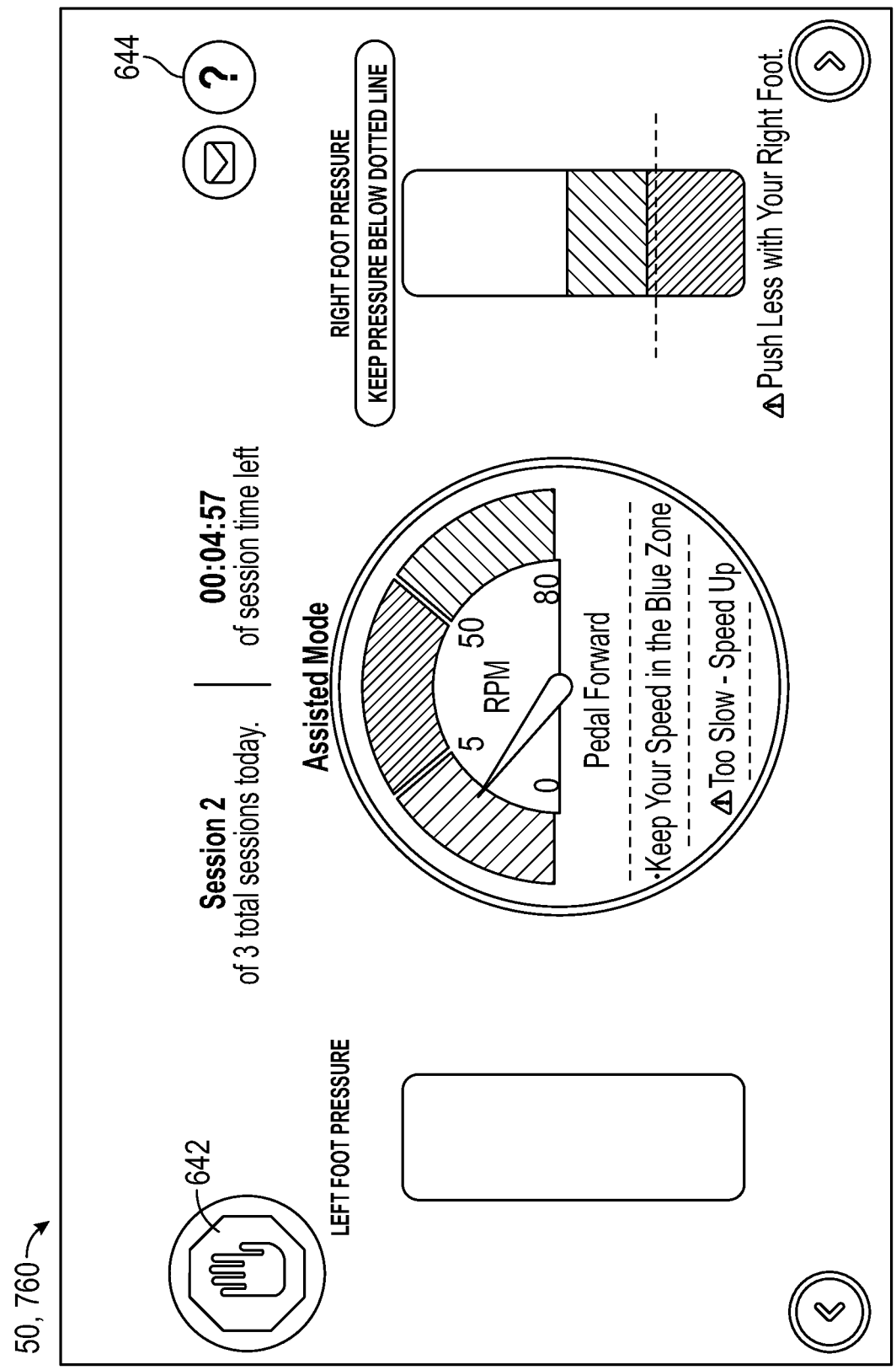
FIG. 8 shows an example embodiment of a session period action screen of a patient interface.

FIG. 8 shows an example embodiment of a session period action screen 760 of the patient interface 50. This screen 760 is displayed while a given session period is in progress. The session period action screen 760 includes an on-screen E-stop control 642 as a stop button for stopping the treatment apparatus 70, which may be present on all screens of the patient interface 50 during the treatment session. The session period action screen 760 also includes a help button 644, which may be present on several or all of the screens of the patient interface 50, and which functions as a manual control for the patient to initiate a telemedicine session with a remote assistant by using the assistant interface 94.

In some embodiments, a telemedicine session with the assistant interface may be initiated by the patient interface 50 in response to a predetermined condition of the treatment apparatus 70. For example, if a patient is unable to meet certain performance criteria, such as RPM or a force upon one of the pedals, or if the patient's performance of an activity using the treatment apparatus 70 is outside of normal use by that patient, then the system 10 may be configured to automatically initiate the telemedicine session wherein an assistant checks to see if the patient needs help.

Figure 9:
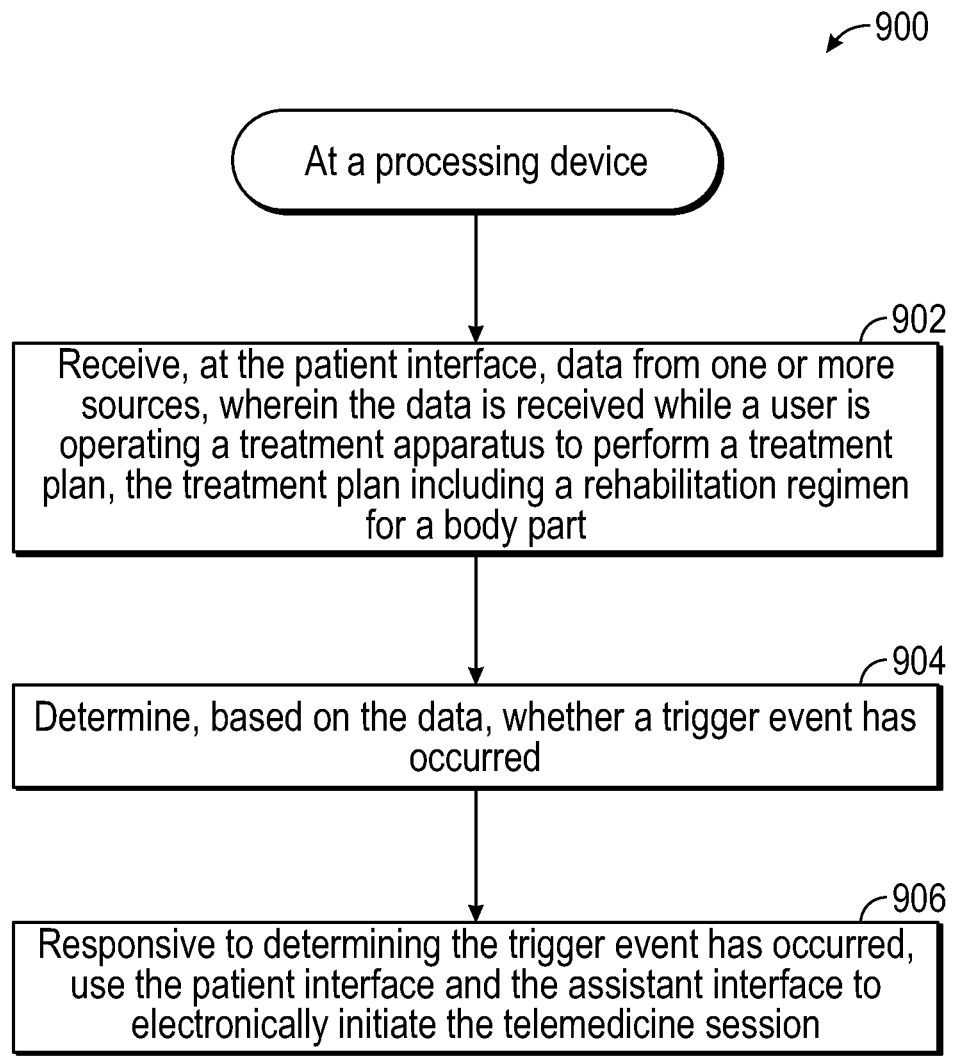
FIG. 9 illustrates example operations of a method for initiating a telemedicine session using a patient interface and an assistant interface according to certain embodiments of this disclosure.

FIG. 9 illustrates example operations of a method 900 for initiating a telemedicine session using a patient interface 50 and an assistant interface 94 according to certain embodiments of this disclosure. The method 900 is performed by processing logic that may include hardware (circuitry, dedicated logic, etc.), software (such as is run on a general purpose computer system or a dedicated machine), or a combination of both. The method 900 and/or each of their individual functions, routines, subroutines, or operations may be performed by one or more processors of a computing device (e.g., any component of FIG. 1, such as patient interface 50, assistant interface server 94, server 30, clinical interface 20, supervisory interface 90, reporting interface 92, treatment apparatus 70, etc.). In certain implementations, the method 900 may be performed by a single processing thread. Alternatively, the method 900 may be performed by two or more processing threads, each thread implementing one or more individual functions, routines, subroutines, or operations of the methods.

For simplicity of explanation, the method 900 is depicted and described as a series of operations. However, operations in accordance with this disclosure can occur in various orders and/or concurrently, and with other operations not presented and described herein. For example, the operations depicted in the method 900 may occur in combination with any other operation of any other method disclosed herein. Furthermore, not all illustrated operations may be required to implement the method 900 in accordance with the disclosed subject matter. In addition, those skilled in the art will understand and appreciate that the method 900 could alternatively be represented as a series of interrelated states via a state diagram or events.

At 902, the processing device may receive, at the patient interface 50, data from one or more sources. In some embodiments, the one or more sources may include a sensor (e.g., pressure or force sensor, goniometer, wearable sensor, etc.), the treatment apparatus 70, an input peripheral (e.g., touchscreen, mouse, keyboard, microphone, camera, etc.) of the patient interface 50, or some combination thereof. In some embodiments, the data may include a sensor measurement (e.g., force measurement from a pressure sensor of the pedal, a range of motion measurement from the goniometer, a vital sign from a wearable, a temperature of the patient from a thermometer, etc.), an answer (e.g., a pain level, whether the exercise is too difficult, etc.) to a question presented on the patient interface 50, a vital sign (e.g., heartrate, blood pressure, etc.), a characteristic of the user, or some combination thereof.

The data may be received while a user (patient) is operating the treatment apparatus 70 to perform a treatment plan. The treatment plan may include a rehabilitation regimen for a body part. In some embodiments, the body part may include at least one of a joint, a bone, a ligament, a tendon, or a muscle group.

At 904, the processing device may determine, based on the data, whether a trigger event has occurred. In some embodiments, the trigger event may include receiving a response to one or more questions presented on the patient interface 50, where the response is an answer to the one or more questions. In some embodiments, the trigger event may include determining a condition of the treatment apparatus 70 (e.g., the patient is not exerting a threshold level of force on the pressure sensor of the pedal, the patient is not able to pedal at a particular range of motion setting, etc.).

At 906, responsive to determining the trigger event has occurred and using the patient interface 50 and the assistant interface 94, the processing device may electronically initiate the telemedicine session. Initiating the telemedicine session may include two-way communication between the patient interface 50 and the assistant interface 94 that triggers an application installed as a stand-alone application or within another application (e.g., website in a web browser) on each of the patient interface 50 and assistant interface 94 to execute computer instructions. The execution of the computer instructions may control the application to initiate the telemedicine session, where the telemedicine session can include audio, visual, audiovisual, or the like. In some embodiments, a portion of a user interface of the application executing on the assistant interface 94 and the patient interface 50 may present a video feed of each respective participant (e.g., the patient feed is presented on the assistant interface 94 and the assistant feed is presented on the patient interface 50).

In some embodiments, the processing device may cause presentation of the data on the assistant interface 94 by transmitting the data to the assistant interface 94. In some embodiments, the processing device may receive, from the assistant interface 94, a telemedicine signal including one of an audio signal, an audiovisual signal, a visual signal, a haptic signal, an environmental change signal, an interface control signal for controlling a function of the patient interface 50, or an apparatus control signal for changing an operating parameter of the treatment apparatus 70.

In some embodiments, the processing device may cause, during the telemedicine session, a patient profile display to be presented on the assistant interface 94. The patient profile display may include information related to the treatment plan for the patient, and the treatment plan may be related to how the patient is intended to use the treatment apparatus.

Any of the systems and methods described in this disclosure may be used in connection with rehabilitation. Rehabilitation may be directed at cardiac rehabilitation, rehabilitation from stroke, multiple sclerosis, Parkinson's disease, a brain injury, a spinal cord injury, a spinal cord disease, a joint injury, a joint disease, or the like. Rehabilitation can further involve muscular contraction improving blood flow and lymphatic flow, engaging the brain and nervous system to control and affect a traumatized area to increase the speed of healing, reversing or reducing pain, reversing or reducing stiffness, recovering range of motion, cardiovascular engagement to stimulate the release of pain blocking hormones and encourage freshly oxygenated blood flow to aid in an overall feeling of well-being. Rehabilitation may be provided for individuals of average height in reasonably good physical condition having no substantial deformities, as well as individuals more typically in need of rehabilitation, such as those that are elderly, obese, injured and/or have a severely limited range of motion. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. Performance of the one or more sets of exercises may be required in order to qualify for an elective surgery, such as a knee replacement. The patient may prepare an area of his or her body for the surgical procedure by performing the one or more sets of exercises, thereby strengthening muscle groups, improving existing muscle memory, reduce pain, reduce stiffness, establishing new muscle memory, enhancing mobility (i.e., improve range of motion), improving blood flow, and/or the like.

In some embodiments, the systems and methods described herein may use artificial intelligence and/or machine learning to generate the treatment plan for a user. Additionally, or alternatively, the systems and methods described herein may use artificial intelligence and/or machine learning to recommend an optimal exercise machine configuration for a user. Additionally, or alternatively, the systems and methods described herein may use artificial intelligence and/or machine learning to control the treatment apparatus during a telemedicine session or not during the telemedicine session. an optimal exercise machine configuration for a user.

Consistent with the above disclosure, the examples of assemblies enumerated in the following clauses are specifically contemplated and are intended as a non-limiting set of examples.

1. A computer-implemented system, comprising: a patient interface comprising an output device and an input device, the output device configured to communicate information to a patient regarding the patient's performance of a treatment plan for the patient, the treatment plan comprising a rehabilitation regimen for a body part; a treatment apparatus configured to be manipulated by the patient for performing the rehabilitation regimen upon the body part; an assistant interface remote from the patient interface and configured to communicate, via a network connection, a telemedicine signal to the patient interface; wherein the telemedicine signal comprises one of an audio signal, an audiovisual signal, a visual signal, a haptic signal, an environmental change signal, an interface control signal for controlling a function of the patient interface, or an apparatus control signal for changing an operating parameter of the treatment apparatus.

2. The computer-implemented system of claim 1, wherein the one of the audio signal, the audiovisual signal, the visual signal, the haptic signal, or the environmental change signal includes a feed from the assistant interface, and the feed is configured to be presented by the output device of the patient interface.

3. The computer-implemented system of claim 1, wherein the telemedicine signal is generated from a prerecorded source, and the telemedicine signal is configured to be presented by the output device of the patient interface.

4. The computer-implemented system of claim 1, wherein the patient interface is configured to transmit an apparatus monitor signal to the assistant interface, and the apparatus monitor signal includes status information related to the treatment apparatus.

5. The computer-implemented system of claim 1, wherein, to effect a change to an operating parameter of the treatment apparatus, the telemedicine signal is configured to comprise the apparatus control signal from the assistant interface.

6. The computer-implemented system of claim 1, wherein the patient interface is configured to provide two-way audio communications, two-way audiovisual communications, two-way visual communications, two-way haptic communications, two-way environmental communications with a person using the assistant interface, or two-way communications using on each side of the communications one of the foregoing means, where the means on one side and the means on the other side are different.

7. The computer-implemented system of claim 1, wherein the patient interface includes a manual control such that the patient uses the assistant interface to initiate a telemedicine session.

8. The computer-implemented system of claim 1, wherein the patient interface is configured to solicit answers to one or more questions from the patient; and wherein predetermined answers to the one or more questions are configured to enable a telemedicine session to be initiated, wherein the telemedicine session uses the assistant interface.

9. The computer-implemented system of claim 1, wherein a predetermined condition of the treatment apparatus causes the patient interface to initiate a telemedicine session, wherein the telemedicine session uses the assistant interface.

10. The computer-implemented system of claim 1, further comprising a clinician interface, wherein such interface includes a protocol management display presenting controls for modifying a treatment protocol within the treatment plan; and wherein the assistant interface is presented on a physical device shared with the clinician interface.

11. The computer-implemented system of claim 1, further comprising a server computer configured to store data related to one of the treatment plan or the patient; and wherein the assistant interface is configured to be in communication with a server for receiving the data related to the one of the treatment plan or the patient.

12. The computer-implemented system of claim 1, wherein the body part comprises at least one of a joint, a bone, a ligament, a tendon, or a muscle group.

13. A system for remote treatment, comprising: a patient interface comprising an output device and an input device for communicating information to and from a patient; a treatment apparatus configured to be manipulated by the patient for performing a rehabilitation regimen upon a body part; an assistant interface configured to communicate a telemedicine signal with the patient interface via a network connection, the telemedicine signal configured to control one of the patient interface or the treatment apparatus; and wherein the patient interface and the treatment apparatus are each configured to operate from a patient location geographically separated from the assistant interface.

14. The system of claim 13, wherein the assistant interface includes a control for changing a setting of one of the patient interface or the treatment apparatus; and wherein the assistant interface is configured to change the setting of the one of the patient interface or the treatment apparatus when the setting cannot be changed by the patient using the patient interface.

15. The system of claim 13, wherein the patient interface is configured to transmit a control signal to the treatment apparatus in response to receiving the telemedicine signal from the assistant interface.

16. The system of claim 13, wherein the body part comprises at least one of a joint, a bone, a ligament, a tendon, or a muscle group.

17. An assistant user interface generated by a computer and comprising: an apparatus control comprising an apparatus status display and an apparatus session control, the apparatus session control configured to adjust an operating parameter of a treatment apparatus, the treatment apparatus configured to be manipulated by a patient for performing a rehabilitation regimen upon a body part; a patient communications control for controlling an audio or an audiovisual communications session with a patient interface, the patient interface configured for use by the patient such that the patient is able to perform the rehabilitation regimen upon the body part.

18. The assistant user interface of claim 17, further comprising a patient interface control presenting information related to the patient interface.

19. The assistant user interface of claim 18, wherein the information related to the patient interface comprises an image presented on a display screen of the patient interface.

20. The assistant user interface of claim 18, wherein the patient interface control further includes a setting control for adjusting a setting of the patient interface.

21. The assistant user interface of claim 17, further comprising a patient profile display presenting biographical information related to the patient using the treatment apparatus.

22. The assistant user interface of claim 17, further comprising a patient profile display presenting information related to a treatment plan for the patient, wherein the treatment plan is related to how the patient is intended to use the treatment apparatus.

23. A method for initiating a telemedicine session using an assistant interface and a patient interface, the method comprising: receiving, at the patient interface, data from one or more sources, wherein the data is received while a user is operating a treatment apparatus to perform a treatment plan, the treatment plan comprising a rehabilitation regimen for a body part; determining, based on the data, whether a trigger event has occurred; and responsive to determining the trigger event has occurred, using the patient interface and the assistant interface to electronically initiate the telemedicine session.

24. The method of claim 23, further comprising: causing presentation of the data on the assistant interface; and receiving, from the assistant interface, a telemedicine signal comprising one of an audio signal, an audiovisual signal, a visual signal, a haptic signal, an environmental change signal, an interface control signal for controlling a function of the patient interface, or an apparatus control signal for changing an operating parameter of the treatment apparatus.

25. The method of claim 23, wherein the one or more sources comprise a sensor, the treatment apparatus, an input peripheral of the patient interface, or some combination thereof.

26. The method of claim 23, wherein the data comprises a sensor measurement, an answer to a question presented on the patient interface, a vital sign, a characteristic of the user, or some combination thereof.

27. The method of claim 23, wherein the trigger event comprises receiving a response to one or more questions presented on the patient interface.

28. The method of claim 23, wherein the trigger event comprises determining a condition of the treatment apparatus.

29. The method of claim 23, wherein the body part comprises at least one of a joint, a bone, a ligament, a tendon, or a muscle group.

30. The method of claim 23, further causing, during the telemedicine session, a patient profile display to be presented on the assistant interface, wherein the patient profile display comprises information related to the treatment plan for the patient, and the treatment plan is related to how the patient is intended to use the treatment apparatus.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A computer-implemented system, comprising:
   a patient interface comprising an output device and an input device, the output device configured to communicate information to a patient regarding the patient's performance of a treatment plan for the patient, the treatment plan comprising a rehabilitation regimen for a body part;
   a treatment apparatus configured to be manipulated by the patient for performing the rehabilitation regimen upon the body part;
   an assistant interface remote from the patient interface and configured to communicate, via a network connection, a telemedicine signal to the patient interface;
   wherein the telemedicine signal comprises one of an audio signal, an audiovisual signal, a visual signal, a haptic signal, an environmental change signal, an interface control signal for controlling a function of the patient interface, or an apparatus control signal for changing an operating parameter of the treatment apparatus.

2. The computer-implemented system of claim 1, wherein the one of the audio signal, the audiovisual signal, the visual signal, the haptic signal, or the environmental change signal includes a feed from the assistant interface, and the feed is configured to be presented by the output device of the patient interface.

3. The computer-implemented system of claim 1, wherein the telemedicine signal is generated from a prerecorded source, and the telemedicine signal is configured to be presented by the output device of the patient interface.

4. The computer-implemented system of claim 1, wherein the patient interface is configured to transmit an apparatus monitor signal to the assistant interface, and the apparatus monitor signal includes status information related to the treatment apparatus.

5. The computer-implemented system of claim 1, wherein, to effect a change to an operating parameter of the treatment apparatus, the telemedicine signal is configured to comprise the apparatus control signal from the assistant interface.

6. The computer-implemented system of claim 1, wherein the patient interface is configured to provide two-way audio communications, two-way audiovisual communications, two-way visual communications, two-way haptic communications, two-way environmental communications with a person using the assistant interface, or two-way communications using on each side of the communications one of the foregoing means, where the means on one side and the means on the other side are different.

7. The computer-implemented system of claim 1, wherein the patient interface includes a manual control such that the patient uses the assistant interface to initiate a telemedicine session.

8. The computer-implemented system of claim 1, wherein the patient interface is configured to solicit answers to one or more questions from the patient; and
   wherein predetermined answers to the one or more questions are configured to enable a telemedicine session to be initiated, wherein the telemedicine session uses the assistant interface.

9. The computer-implemented system of claim 1, wherein a predetermined condition of the treatment apparatus causes the patient interface to initiate a telemedicine session, wherein the telemedicine session uses the assistant interface.

10. The computer-implemented system of claim 1, further comprising a clinician interface, wherein such interface includes a protocol management display presenting controls for modifying a treatment protocol within the treatment plan; and
    wherein the assistant interface is presented on a physical device shared with the clinician interface.

11. The computer-implemented system of claim 1, further comprising a server computer configured to store data related to one of the treatment plan or the patient; and
    wherein the assistant interface is configured to be in communication with a server for receiving the data related to the one of the treatment plan or the patient.

12. The computer-implemented system of claim 1, wherein the body part comprises at least one of a joint, a bone, a ligament, a tendon, or a muscle group.

13. A system for remote treatment, comprising:
a patient interface comprising an output device and an input device for communicating information to and from a patient;
a treatment apparatus configured to be manipulated by the patient for performing a rehabilitation regimen upon a body part;
an assistant interface configured to communicate a telemedicine signal with the patient interface via a network connection, the telemedicine signal configured to control one of the patient interface or the treatment apparatus; and
wherein the patient interface and the treatment apparatus are each configured to operate from a patient location geographically separated from the assistant interface.

14. The system of claim 13, wherein the assistant interface includes a control for changing a setting of one of the patient interface or the treatment apparatus; and
wherein the assistant interface is configured to change the setting of the one of the patient interface or the treatment apparatus when the setting cannot be changed by the patient using the patient interface.

15. The system of claim 13, wherein the patient interface is configured to transmit a control signal to the treatment apparatus in response to receiving the telemedicine signal from the assistant interface.

16. The system of claim 13, wherein the body part comprises at least one of a joint, a bone, a ligament, a tendon, or a muscle group.

17. An assistant user interface generated by a computer and comprising:
an apparatus control comprising an apparatus status display and an apparatus session control, the apparatus session control configured to adjust an operating parameter of a treatment apparatus, the treatment apparatus configured to be manipulated by a patient for performing a rehabilitation regimen upon a body part;
a patient communications control for controlling an audio or an audiovisual communications session with a patient interface, the patient interface configured for use by the patient such that the patient is able to perform the rehabilitation regimen upon the body part.

18. The assistant user interface of claim 17, further comprising a patient interface control presenting information related to the patient interface.

19. The assistant user interface of claim 18, wherein the information related to the patient interface comprises an image presented on a display screen of the patient interface.

20. The assistant user interface of claim 18, wherein the patient interface control further includes a setting control for adjusting a setting of the patient interface.

21. The assistant user interface of claim 17, further comprising a patient profile display presenting biographical information related to the patient using the treatment apparatus.

22. The assistant user interface of claim 17, further comprising a patient profile display presenting information related to a treatment plan for the patient, wherein the treatment plan is related to how the patient is intended to use the treatment apparatus.

23. A method for initiating a telemedicine session using an assistant interface and a patient interface, the method comprising:
receiving, at the patient interface, data from one or more sources, wherein the data is received while a user is operating a treatment apparatus to perform a treatment plan, the treatment plan comprising a rehabilitation regimen for a body part;
determining, based on the data, whether a trigger event has occurred; and
responsive to determining the trigger event has occurred, using the patient interface and the assistant interface to electronically initiate the telemedicine session.

24. The method of claim 23, further comprising:
causing presentation of the data on the assistant interface; and
receiving, from the assistant interface, a telemedicine signal comprising one of an audio signal, an audiovisual signal, a visual signal, a haptic signal, an environmental change signal, an interface control signal for controlling a function of the patient interface, or an apparatus control signal for changing an operating parameter of the treatment apparatus.

25. The method of claim 23, wherein the one or more sources comprise a sensor, the treatment apparatus, an input peripheral of the patient interface, or some combination thereof.

26. The method of claim 23, wherein the data comprises a sensor measurement, an answer to a question presented on the patient interface, a vital sign, a characteristic of the user, or some combination thereof.

27. The method of claim 23, wherein the trigger event comprises receiving a response to one or more questions presented on the patient interface.

28. The method of claim 23, wherein the trigger event comprises determining a condition of the treatment apparatus.

29. The method of claim 23, wherein the body part comprises at least one of a joint, a bone, a ligament, a tendon, or a muscle group.

30. The method of claim 23, further causing, during the telemedicine session, a patient profile display to be presented on the assistant interface, wherein the patient profile display comprises information related to the treatment plan for the patient, and the treatment plan is related to how the patient is intended to use the treatment apparatus.

* * * * *